United States Patent [19]

D'Silva

[11] Patent Number: 4,469,688
[45] Date of Patent: Sep. 4, 1984

[54] PESTICIDAL CYANO ENOL PHOSPHATES

[75] Inventor: Themistocles D. J. D'Silva, Chapel Hill, N.C.

[73] Assignee: Union Carbide Corporation, Danbury, Conn.

[21] Appl. No.: 393,552

[22] Filed: Jun. 30, 1982

[51] Int. Cl.³ .................. A01N 57/14; C07F 9/165
[52] U.S. Cl. .................................. 424/210; 260/940
[58] Field of Search ..................... 260/940; 424/210

[56] References Cited

U.S. PATENT DOCUMENTS 3,763,285 10/1973 Riebel et al. .................... 260/940
3,775,517 11/1973 Riebel et al. .................... 260/940
3,892,823 7/1975 Maurer et al. ................... 260/940

FOREIGN PATENT DOCUMENTS 2053713 5/1972 Fed. Rep. of Germany .
1233118 5/1971 United Kingdom .

OTHER PUBLICATIONS

Nishizawa, "Agr. Biol. Chem.," vol. 25, No. 1, (1961), pp. 61–65.

Primary Examiner—Anton H. Sutto
Attorney, Agent, or Firm—J. A. Shedden

[57] ABSTRACT

Novel cyano enol phosphates are provided which have utility as pesticides.

21 Claims, No Drawings

PESTICIDAL CYANO ENOL PHOSPHATES

This invention relates to novel insecticidal and miticidal cyano enol phosphates. This invention also relates to pesticidal compositions for controlling insects and mites, as well as to methods of controlling insects and mites by subjecting them to an insecticidally or miticidally effective amount of a compound of this invention.

The novel compounds of this invention are compounds of the formula:

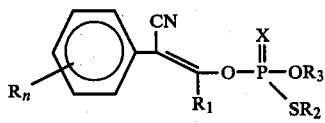

wherein:
R is hydrogen, $C_1$ to $C_4$ alkyl, $C_1$ to $C_4$ alkylthio, $C_1$ to $C_4$ alkoxy, trihalomethyl, di- or trifluoromethoxy or halogen.

$R_1$ is hydrogen, unsubstituted or alkyl or halogen substituted cycloalkyl, alkenyl, alkenylcycloalkyl, alkynyl, trihaloalkyl, alkoxycarbonyl, benzyl, $C_1$ to $C_{10}$ alkyl, alkoxy $C_1$ to $C_{10}$ alkyl, haloalkoxy $C_1$ to $C_{10}$ alkyl, alkoxycarbonyl $C_1$ to $C_{10}$ alkyl, alkoxyphenyl, haloalkoxyphenyl or alkoxycarbonylphenyl;

X is oxygen or sulfur;

n is 0 to 5; and $R_2$ and $R_3$ are individually $C_1$ to $C_6$ alkyl.

Both geometric isomers are considered to be within the scope of this invention.

Generally, the preferred compounds of this invention are those wherein:
X is oxygen;
$R_2$ is propyl; and
$R_3$ is ethyl.

The more preferred compounds of this invention are those "preferred" wherein:

| R | $R_1$ |
|---|---|
| 2-$CH_3$ | —$CH_2$—$C(CH_3)_2$—$CH_2CO_2C_2H_5$ |
| 2-$CH_3$ | —$CH_2$—$CH(CH_3)_2$ |
| 2-$CH_3$ | —$CH(CH_3)_2$ |
| 2-$CH_3$ | —$CH_3$ |
| 2,4-Cl | —$CH(CH_3)_2$ |
| 2-$CH_3$ | —CH——CH($CH_3)_2$ (with epoxide-Cl group) |

The novel cyano enol phosphates of this invention can be conveniently prepared by the general reaction methods or a modification thereof set forth below.

In the following reaction schemes R, $R_1$, $R_2$, $R_3$, X and n have the meanings given in the generic formula (vide supra).

METHOD I

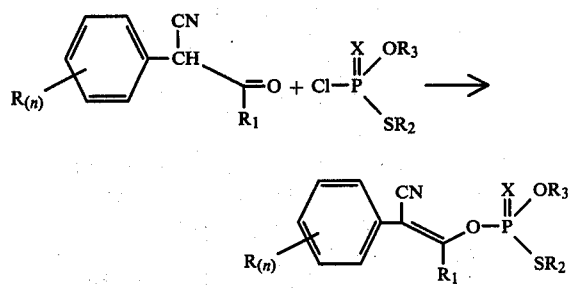

Method I is a one-step reaction wherein stoichiometric amounts of the cyano ketone and an appropriate chlorophosphate compound are reacted in an inert solvent in the presence of a stoichiometric amount of an acid acceptor.

Methods II and III illustrated by the general schemes below, are two-step methods wherein an appropriate cyano ketone is reacted with an appropriate dihalophosphorous compound in the presence of a stoichiometric amount of an acid acceptor.

METHOD II

Step A

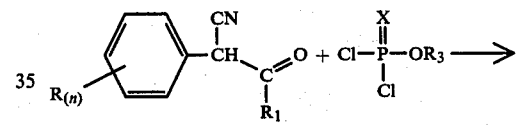

Step B

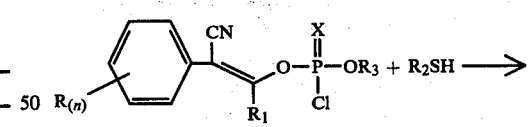

METHOD III

Step A

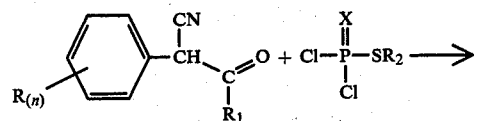

-continued

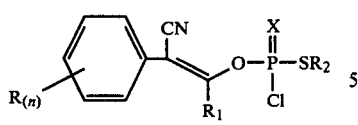

Step B

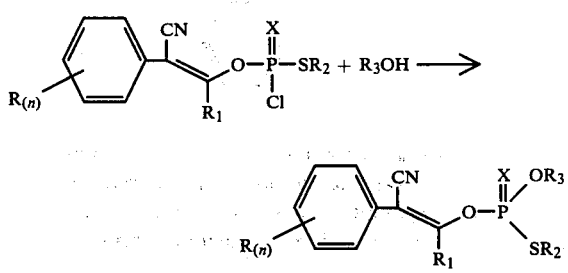

The reactions in Steps A and B in the methods II and III, are conducted in the presence of an acid acceptor which can be either an organic or inorganic base. The organic bases may be selected from among the tertiary amines such as trimethylamine, triethylamine, pyridine, 4-dimethylamino pyridine, 1,4-diazabicyclo [2.2.2] octane and the like. Examples of inorganic bases which may be used are sodium carbonate, potassium carbonate, sodium hydroxide, sodium hydride and the like.

When an inorganic base is used, phase transfer agents may be used to facilitate the transfer of the base across the organic/inorganic phase interface. Illustrative of the useful phase transfer agents are crown ether compounds, quaternary ammonium halide compounds and the like.

Illustrative of suitable inert solvents are aromatic hydrocarbons such as toluene, xylene, naphthalene, tetralin, and the like; aliphatic chlorinated hydrocarbons such as methylene chloride, chloroform, carbon tetrachloride and mono-, di- and tri-chloroethylene; low boiling aliphatic ketones and nitriles such as acetone, methyl ethyl ketone, methyl isopropyl ketone, methyl isobutyl ketone, acetonitrile, and propionitrile; and ethers such as diethyl ether, tert-butylmethyl ether, dioxane and tetrahydrofuran.

The reactions may also be conducted in a solvent which also functions as an acid acceptor such as multi-functional solvents like pyridine, alpha-picoline, N,N-dimethyl aniline, and any lutidine, collidine or any like aromatic or heterocyclic tertiary amine compound.

The reactions may be conducted over a wide range of temperature and pressures. It is preferable to conduct them at temperatures between −20° C. and 120° C. and at atmospheric or autogeneous pressure.

The phosphorus halides and dihalides used as reactants in the above methods are known materials which can be obtained commercially or prepared in accordance with conventional methods known to those skilled in the art.

The cyano-ketone intermediates used as reactants can be obtained by methods disclosed in J. Org. Chem. 35 (7), 2215 (1970), U.S. Pat. No. 4,256,658.

The following examples are illustrative of the methods of preparing the novel compounds of this invention:

Example I

Preparation of alpha-(3-Methyl phenyl)-3-methylbutanoyl acetonitrile

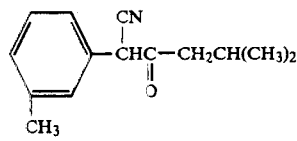

To a solution of 2.99 g (0.13 g. atm) of sodium in 50 ml of absolute ethanol, heated to 60° C., was added 11.81 g (0.09 m) of 3-methyl-benzyl cyanide followed by the slow addition, over a period of 20 minutes of 31.27 g (0.24 m) of ethyl isovalerate. The reaction mixture was heated under reflux overnight (18 hrs.). During this period the color of the solution turned from yellow to dark orange. After approximately 70 ml of solvent and excess of ethyl valerate was removed by distillation, 75 ml of toluene was added and additional 30 ml of the solvent was removed by heating the mixture to 112° C. The reaction mixture was cooled, diluted with 100 ml of toluene and was washed twice with water. The aqueous extracts were combined and acidified with 6N hydrochloric acid. The product was extracted in 300 ml of methylene chloride. The organic extract was washed with water, dried over magnesium sulfate and was concentrated under vacuum to afford 18.56 g of orange colored oil. Crystallization from ethyl acetate hexane solution afforded 14.0 g. of a white solid. m.p. 46.5°–50° C.

Calcd. for $C_{14}H_{17}NO$: C, 78.10; H, 7.96; N, 6.51. Found: C, 77.53; H, 8.22; N, 5.94.

EXAMPLE II

Preparation of alpha-(2-Methyl phenyl) benzoyl acetonitrile

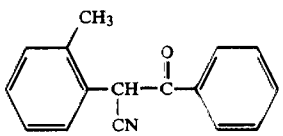

By following the procedure in Example I, 13.12 g (0.1 m) of 2-methyl benzyl cyanide, 16.52 g. (0.11 m) of ethyl benzoate and 2.99 g (0.13 g atom) of sodium in 100 ml of ethanol, afforded 2.1 g. of a viscous oil.

Calcd. for $C_{16}H_{13}N$: C, 81.67; H, 5.57; N, 5.95. Found: C, 81.29; H, 5.53; N, 6.11.

EXAMPLE III

Preparation of O-Ethyl-S-propyl-O-(1-(2,4-dichloro phenyl)-1-cyano-4-methyl-1-penten-2-yl)-thiophosphoric acid ester

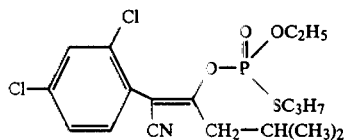

To a cold solution of 5.37 g (0.0199 m) of alpha-(2,4 dichloro phenyl)-3-methyl butanoyl acetonitrile dissolved in 50 ml of acetonitrile was added 4.46 g (0.022 m) of O-ethyl-S-propylthio chlorophosphate followed by dropwise addition of 2.01 g (0.0199 m) of triethylamine. The reaction mixture was stirred for 1 hour at 0° C. and for 16 hours at ambient temperatures. The solvent was removed under reduced pressure. The residual semisolid was taken in 150 ml of ethyl acetate and 25 ml of water. The organic extract was further washed with water, dried over magnesium sulfate and concentrated under reduced pressure to afford 5.9 g (68 percent) of viscous oil.

Calcd. For $C_{18}H_{24}Cl_2NO_3PS$: C, 49.55; H, 5.54; N, 3.21. Found: C, 49.39; H, 5.98; N, 2.82.

EXAMPLE IV

Preparation of
O-Ethyl-S-propyl-O-(1-(2-methylphenyl)-1-cyano-4,4-dimethyl-5-ethoxycarbonyl-penten-2-yl) thiophosphoric acid ester

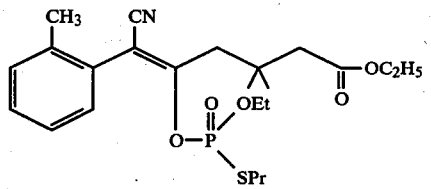

To a cold (0° C.) solution of 14.37 g (0.05 m) of ethyl-6-cyano-6-(2'-methylphenyl)-3,3-dimethyl-5-keto hexanoate in 100 ml of methylene chloride was added 10.14 g (0.05 m) of O-ethyl-S-propyl chlorophosphate dissolved in 25 ml of methylene chloride. Maintaining the temperature at 0° C., 5.06 g (0.05 m) or triethylamine was added dropwise over a period of 10 minutes. The reaction mixture was stirred at ambient temperature for 48 hours and under reflux for 24 hours. When it was cooled to ambient temperature it was diluted with 50 ml of methylene chloride and the organic mixture was washed successively with 50 ml water, 2×40 ml of cold 5 percent sodium hydroxide, 2×40 ml of cold 5 percent hydrochloric acid and with water until neutral. On drying and concentrating under reduced pressure it afforded 17.2 g (73.56 percent) of a yellow colored oil. The NMR and I.R were consistent with the structure.

Calcd. for $C_{23}H_{34}NO_5PS$: C, 59.08; H, 7.33; N, 2.99. Found: C, 59.57; H, 7.45; N, 3.11.

The following compounds are illustrative of this invention all of which can be conveniently prepared by the processes of this invention simply by selecting the appropriate starting materials.

O-Ethyl-S-propyl-O-(2-phenyl-2-cyano vinyl)-thiophosphoric acid ester.

O-Ethyl-S-propyl-O-(2-methyl phenyl)-2-cyano-vinyl)-thiophosphoric acid ester.

O-Ethyl-S-propyl-O-(1-(2-methylphenyl)-1-cyanopropen-2-yl)thiophosphoric acid ester.

O-Ethyl-S-propyl-O-(1-phenyl-1-cyanopropen-2-yl)thiophosphoric acid ester.

O-Ethyl-S-propyl-O-(1,2-diphenyl-1-cyano vinyl) thiophosphoric acid ester.

O-Ethyl-S-propyl-O-(1-(2-,4-dichlorophenyl)-1-cyanopropen-2-yl) thiophosphoric acid ester.

O-Ethyl-S-propyl-O-(1-(4-trifluoromethyl phenyl)-1-cyano-3-methyl buten-2-yl) thiophosphoric acid ester.

O-Ethyl-S-propyl-O-(1-(4-methoxyphenyl)-1-cyano-2-phenylvinyl) thiophosphoric acid ester.

O-Ethyl-S-propyl-O-(1-(4-chlorophenyl)-1-cyano octen-2-yl) thiophosphoric acid ester.

O-Ethyl-S-propyl-O-(1-(4-chlorophenyl) 1-cyano-3-methyl penten-2-yl) thiophosphoric acid ester.

O-Ethyl-S-propyl-O-(1-(2-methyl phenyl) 1-cyano decen-2-yl) thiophosphoric acid ester.

O-Ethyl-S-propyl-O-(1-(4-difluoromethoxy phenyl)-1-cyano-4-methyl penten-2-yl) thiophosphoric acid ester.

O-Ethyl-S-propyl-O-(1-(4-methylthiophenyl)-1-cyano-3-methyl buten-2-yl) thiophosphoric acid ester.

O-Ethyl-S-propyl-O-(1-(2-methylphenyl) 1-cyano-3-(4-difluoromethoxy phenyl)-4-methyl penten-2-yl) thiophosphoric acid ester.

O-Ethyl-S-propyl-O-(1-(2-methylphenyl) 1-cyano-3-(4-trifluoromethoxy phenyl)-4-methyl penten-2-yl) thiophosphoric acid ester.

O-Ethyl-S-propyl-O-(1-(2-methylphenyl)1-cyano-2-cyclopropyl vinyl) thiophosphoric acid ester.

O-Ethyl-S-propyl-O-(1-(4-chlorophenyl) 1-cyano-2-(1-propynyl)vinyl) thiophosphoric acid ester.

O-Ethyl-S-propyl-O-(1-(4-chlorophenyl) 1-cyano-2-(2,2-dimethyl-3-isobutenyl cyclopropyl)vinyl) thiophosphoric acid ester.

O-Ethyl-S-propyl-O-(1-(4-chlorophenyl) 1-cyano-2-(2,2-dimethyl-3-(2,2-dichloro vinyl) cyclopropyl)vinyl) thiophosphoric acid ester.

O-Ethyl-S-propyl-O-(1-(2-methylphenyl)-1-cyano-2-trifluoromethyl vinyl) thiono thiophosphoric acid ester.

O-Ethyl-S-propyl-o-(1-(4-methylphenyl)-1-cyano-2-ethoxycarbonyl vinyl) thiono thiophosphoric acid ester.

O-Ethyl-S-propyl-O-(1-(4-chloro phenyl)-1-cyano-4-methyl 1,3-pentadien-2-yl) thiono thiophosphoric acid ester.

O-Ethyl-S-propyl-O-(1-(2-methyl phenyl)-1-cyano-2-tetramethyl cyclopropyl vinyl) thiophosphoric acid ester.

Selected species of the new compounds were evaluated to determine their pesticidal activity against mites, an aphid, a caterpillar, a beetle, and a fly.

Suspensions of the test compounds were prepared by dissolving one gram of compound in 50 ml of acetone in which had been dissolved 0.1 g (10 percent of the weight of the compound) of an alkylphenoxy polyethoxyethanol surfactant, as an emulsifying or dispersing agent. The resulting solution was mixed into 150 ml of water to give roughly 200 ml of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 68°–70° F. and 50±5 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation or as adjusted for $LD_{50}$ data.

The potted plants (one pot per compound tested) infested with 100–150 aphids were placed on a revolving turntable and sprayed with 100–110 milliliters of test compound formulation by use of a DeVilbiss spray gun set at 40 psia air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 68°–70° F. and 50±5 percent, respectively. Aphids which fell onto the paper and were unable to remain standing after being unrighted were considered dead. Aphids remaining on the plant were observed closely for movement and those which were unable to move the length of the body upon stimulation by prodding were considered dead. Percent morality was recorded for various concentration levels.

Southern Armyworm Leaf Spray Bait Test

Larvae of the southern armyworm (*Spodoptera eridania*, (Cram.)), reared on Tendergreen bean plants at a temperature of 80°+5° F. and a relative humidity of 50±5 percent, constituted the test insects.

The test compounds were formulated by diluting the stock suspension with water to give a suspension containing 500 parts of test compound per million parts of final formulation or as adjusted for $LD_{50}$ data. Potted Tendergreen bean plants of standard height and age were placed on a revolving turntable and sprayed with 100–110 milliliters of test compound formulations by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dished were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulations or as adjusted for $LD_{50}$ data. Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dished were closed. The closed dishes were labeled and held at a temperature of 80°±5° F., for three days. Although the larvae could easily consume the leaf within 24 to 48 hours, no more food was added. Larvae which were unable to move the length of the body even upon stimulation, were considered dead.

Mite Foliage Spray Test

Adults and nymphal stage of the two-spotted mite (*Tetranychus urticae*, Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 mites, a sufficient number for testing, were transferred from the excised leaves to the fresh plants in a period of twenty-four hours. Following the twenty-four hour transfer period, the excised leaves were removed from the infested plants. The test compounds were formulated by diluting the stock suspension with water to give a suspension containing 500 parts of test compound per million parts of final formulation or as adjusted for $LD_{50}$ data. The potted plants (one pot per compound) were placed on a revolving turntable and sprayed with 100–110 milliliters of test compound formulation by use of a Devilbiss spray gun set at 40 psig air pressure. This application, which lasted 25 seconds, was sufficient to wet the plants to run-off. As a control, 100–110 milliliters of a water solution containing acetone and emulsifier in the same concentrations as the test compound formulations, but containing no test compound, were also sprayed on infested plants. The sprayed plants were held a 80±5 percent relative humidity for six days, after which a mortality count of motile forms was made. Microscopic examination for motile forms was made on the leaves of the test plants. Any individual which was capable of locomotion upon prodding was considered living.

Fly Bait Test

Four to six day old adult house flies (*Musca domestica*, L.), reared according to the specifications of the Chemical Specialties Manufacturing Association (Blue Book, McNair-Dorland Co., NY 1954; pages 243–244, 261) under controlled conditions of 80°±5° F. and 50±5 percent relative humidity, were the test insects. The flies were immobilized by anesthetizing with carbon dioxide and twenty-five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation by weight or as adjusted for $LD_{50}$ data. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty-four hours, at a temperature of 80°±5° F. and a relative humidity of 50±5 percent.

Flies which showed no sign of movement on prodding were considered dead.

The results of these tests together with physical properties of the tested compounds are set forth in Table I below. In these tests the pesticidal activity of the compounds at the indicated dosage rate against aphid, mite, Southern Armyworm, Bean Beetle, and housefly was rated as follows:

A=excellent control (70–100% kill) at 500 ppm
B=partial control (41–69% kill) at 500 ppm
C=no control (0–40% kill) at 500 ppm The compounds comtemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In preparation of wettable powder, dust or granulated compositions, the active ingredient is dispersed in and on an appropriately divided solid carrier such as clay, talc, bentonite, diatomaceous earth, fullers, earth, and the like. In the formulation of the wettable powders the aforementioned dispersing agents as well as lignosulfonates can be included.

The required amount of the toxicants comtemplated herein may be applied per acre treated in from 1 to 200 gallons or more of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein control the population of insects and mites and insects upon plants or other material to which the pesticides are applied. Generally, when used in sufficient amount to kill or repel the insects, they do not burn or injure the plant. The toxicants are compatible with substantially any other constituents of the spray schedule, and they may be used in the soil, upon the seeds or the roots of the plants without injuring either the seeds or roots of plants. They may also be used in combination with other pesticidally active compounds or synergists.

TABLE I

Biological and Analytical Properties of the Compounds of this Invention $$\underset{R_1}{\underset{|}{\text{Ar}}}\text{—O—}\overset{X}{\underset{\|}{P}}\text{(OC}_2\text{H}_5\text{)(SC}_3\text{H}_7\text{)}$$

(where Ar = substituted phenyl bearing CN and R groups)

| Example | R | R₁ | X | Analytical | Bean Aphid | 2-Sp. Mite | Southern Armyworm | Mexican Bean Bettle | House Fly |
|---|---|---|---|---|---|---|---|---|---|
| 1 | 2-CH₃ | H | O | C₁₅H₂₀NO₃PS<br>Calc.: C,55.37;H,6.19;N,4.30<br>Found: C,54.43;H,6.39;N,4.02 | A | A | B | C | C |
| 2 | 2-CH₃ | —CH=C(CH₃)₂ | O | C₁₉H₂₆NO₃PS<br>Calc.: C,60.14;H,6.91;N,3.69<br>Found: C,60.89;H,6.98;N,3.69 | A | A | A | A | A |
| 3 | 2-CH₃ | —CH=C(CH₃)₂ | S | C₁₉H₂₆NO₂PS₂<br>Calc.: C,57.70;H,6.63;N,3.54<br>Found: C,57.93;H,6.89;N,3.59 | A | A | A | A | C |
| 4 | 2-CH₃ | —CH₂—CH(CH₃)₂ | O | C₁₉H₂₈NO₃PS<br>Calc.: C,59.82;H,7.39;N,3.67<br>Found: C,58.38;H,7.61;N,3.31 | A | A | A | A | A |
| 5 | 2,4-di-CH₃ | —CO₂C₂H₅ | O | C₁₉H₂₆NO₅PS<br>Calc.: C,55.46;H,6.37;N,3.40<br>Found: C,54.19;H,6.67;N,3.12 | C | A | C | A | C |
| 6 | 4-C₂H₅ | —CO₂C₂H₅ | O | C₁₉H₂₆NO₅PS<br>Calc.: C,55.46;H,6.37;N,3.40<br>Found: C,54.42;H,6.66;N,3.12 | C | C | C | B | C |
| 7 | 2-CH₃ | —CF₃ | O | C₁₆H₁₉F₃NO₃PS<br>Calc.: C,48.85;H,4.87;N,3.56<br>Found: C,48.06;H,5.05;N,3.30 | C | B | C | C | C |
| 8 | 2-CH₃ | —CH(CH₃)₂ | O | C₁₈H₂₆NO₃PS<br>Calc.: C,58.84;H,7.13;N,3.81<br>Found: C,59.19;H,7.22;N,3.75 | A | A | A | A | A |
| 9 | 2-CH₃ | —CH₃ | O | C₁₆H₂₂NO₃PS<br>Calc.: C,56.62;H,6.53;N,4.13<br>Found: C,56.90;H,6.68;N,4.02 | A | A | A | A | A |
| 10 | 3-CH₃ | —CH₂CH(CH₃)₂ | O | C₁₉H₂₈NO₃PS<br>Calc.: C,59.82;H,7.40;N,3.67<br>Found: C,59.68;H,7.46;N,3.70 | A | A | A | A | A |
| 11 | 4-Cl | —CH₂CH(CH₃)₂ | O | C₁₈H₂₅ClNO₃PS<br>Calc.: C,53.79;H,6.27;N,3.48<br>Found: C,53.95;H,6.44;N,3.54 | A | A | A | A | A |

TABLE I-continued

Biological and Analytical Properties of the Compounds of this Invention $$\text{R-C}_6\text{H}_4\text{-C(CN)(R}_1)\text{-O-P(=X)(OC}_2\text{H}_5)(\text{SC}_3\text{H}_7)$$

| Example | R | $R_1$ | X | Analytical | Bean Aphid | 2-Sp. Mite | Southern Armyworm | Mexican Bean Beetle | House Fly |
|---|---|---|---|---|---|---|---|---|---|
| 12 | 3-CH$_3$ | —CH(CH$_3$)$_2$ | O | C$_{18}$H$_{26}$NO$_3$PS<br>Calc.: C,58.84;H,7.13;N,3.81<br>Found: C,58.47;H,7.18;N,3.94 | A | A | A | B | A |
| 13 | 4-CH$_3$ | —CH$_2$CH(CH$_3$)$_2$ | O | C$_{19}$H$_{28}$NO$_3$PS<br>Calc.: C,59.82;H,7.40;N,3.61<br>Found: C,59.99;H,7.60;N,3.61 | A | A | A | A | A |
| 14 | 4-CH$_3$ | —CH$_2$CH(CH$_3$)$_2$ | S | C$_{19}$H$_{28}$NO$_2$PS$_2$<br>Calc.: C,57.41;H,7.10;N,3.52<br>Found: C,58.17;H,7.01;N,3.79 | C | A | A | C | C |
| 15 | 2,4-di-Cl | —CH(CH$_3$)$_2$ | O | C$_{17}$H$_{22}$Cl$_2$NO$_3$PS<br>Calc.: C,48.35;H,5.25;N,3.32<br>Found: C,48.58;H,5.33;N,3.32 | A | A | A | A | A |
| 16 | 4-Cl | —CH(CH$_3$)$_2$ | O | C$_{17}$H$_{23}$ClNO$_{23}$PS<br>Calc.: C,52.64;H,5.98;N,3.61<br>Found: C,52.72;H,6.17;N,3.63 | A | A | A | A | A |
| 17 | H | —CH$_2$CH(CH$_3$)$_2$ | O | C$_{18}$H$_{26}$NO$_3$PS<br>Calc.: C,58.84;H,7.31;N,3.81<br>Found: C,58.57;H,7.13;N,3.95 | A | A | A | A | A |
| 18 | 4-Cl | —C$_6$H$_5$ | O | C$_{20}$H$_{21}$ClNO$_3$PS<br>Calc.: C,56.94;H,5.01;N,3.32<br>Found: C,57.30;H,5.06;N,3.30 | A | A | A | A | A |
| 19 | H | —CH(CH$_3$)$_2$ | O | C$_{17}$H$_{24}$NO$_3$PS<br>Calc.: C,57.77;H,6.84;N,3.96<br>Found: C,57.92;H,6.98;N,3.85 | A | A | A | A | A |
| 20 | 2-CH$_3$ | —C$_6$H$_5$ | O | C$_{21}$H$_{24}$NO$_3$PS<br>Calc.: C,62.83;H,6.03;N,3.49<br>Found: C,62.71;H,6.14;N,3.43 | A | A | A | A | A |
| 21 | 4-Cl | 2-Cl—C$_6$H$_4$ | O | C$_{20}$H$_{20}$Cl$_2$NO$_3$PS<br>Calc.: C,52.64;H,4.42;N,3.07<br>Found: C,53.31;H,4.30;n,3.19 | A | A | A | A | A |
| 22 | 4-Cl | 4-Cl—C$_6$H$_4$ | O | C$_{20}$H$_{20}$Cl$_2$NO$_3$PS<br>Calc.: C,52.64;H,4.42;N,3.07<br>Found: C,51.31;H,4.49;N,2.31 | A | A | A | A | A |
| 23 | 2-CH$_3$ | —(CH$_2$)$_2$CO$_2$C$_2$H$_5$ | O | C$_{20}$H$_{28}$NO$_5$PS<br>Calc.: C,56.46;H,6.63;N,3.29<br>Found: C,57.33;H,6.67;N,3.49 | A | A | A | A | A |
| 24 | 2-CH$_3$ | 2-CH$_3$CO$_2$C$_6$H$_4$ | O | C$_{23}$H$_{26}$NO$_5$PS<br>Calc.: C,60.12;H,5.70;N,3.05<br>Found: C,58.26;H,5.75;N,2.96 | A | A | A | A | A |
| 25 | 2-CH$_3$ | —(CH$_2$)$_4$CO$_2$CH$_3$ | O | C$_{21}$H$_{30}$NO$_5$PS<br>Calc.: C,57.39;H,6.88;N,3.19<br>Found: C,54.16;H,6.98;N,2.97 | A | A | A | A | A |
| 26 | 2-CH$_3$ | cyclopropyl with CH$_3$, CH$_3$, =CCl$_2$ | O | C$_{22}$H$_{28}$Cl$_2$NO$_3$PS<br>Calc.: C,54.10;H,5.78;N,2.87<br>Found: C,54.20;H,5.73;N,3.07 | A | A | A | A | A |
| 27 | 2-CH$_3$ | C(CH$_3$)$_2$-(4-Cl-C$_6$H$_4$) | O | C$_{25}$H$_{31}$ClNO$_3$PS<br>Calc.: C,61.03;H,6.35;N,2.85<br>Found: C,61.14;H,6.34;N,2.88 | A | A | A | A | A |
| 28 | 2-CH$_3$ | CH$_2$C(CH$_3$)$_2$CH$_2$CO$_2$C$_2$H$_5$ | O | C$_{23}$H$_{24}$NO$_5$PS<br>Calc.: C,59.08; H, 7.33; N, 2.99<br>Found: C, 59.57; H, 7.45; N, 3.11 | A | A | A | A | A |
| 29 | 2,4-di-Cl | CH$_2$CH(CH$_3$)$_2$ | O | C$_{18}$H$_{24}$Cl$_2$NO$_3$PS<br>Calc.: C, 49.55; H, 5.54; N, 3.21<br>Found: C, 49.39; H, 5.98; N, 2.82 | A | A | A | A | A |

In Table II, the activity of representative compounds of the instant invention is compared to a related prior art compound (U.S. Pat. No. 3,892,823) and a commercial acaricide standard (Kelthane). With respect to the two-spotted mites, the compounds of this invention have significantly enhanced activity over the comparisons.

TABLE II
TWO-SPOTTED MITE (TETRANYCHUS URTICAE) TEST

| Active Compound | Concentration in p.p.m. | Percent Kill After 4-days |
|---|---|---|
| [Structure: O-P(=S)(OC₂H₅)(SC₃H₇) phenyl-C(CN)=CH] (U.S. Pat. No. 3,892,823) | 500<br>125<br>31 | 80<br>49<br>22 |
| [Structure: 1,1-bis(chlorophenyl)-2,2,2-trichloroethanol (Kelthane)] | 40<br>20 | 100<br>54 |
| [Structure: CH₃-phenyl-C(CN)=C(CH(CH₃)CH₃)-O-P(=O)(OC₂H₅)(SC₃H₇)] | 500<br>125<br>31<br>8 | 100<br>100<br>100<br>100 |
| [Structure: CH₃-phenyl-C(CN)=C(CH(CH₃)CH₃)-O-P(=O)(OC₂H₅)(SC₃H₇)] | 500<br>125<br>31<br>8 | 100<br>100<br>98<br>60 |
| [Structure: phenyl-C(CN)=C(CH(CH₃)CH₃)-O-P(=O)(OC₂H₅)(SC₃H₇)] | 500<br>125<br>31<br>8 | 100<br>100<br>100<br>67 |

In Table III, the activity of representative cyano-enol-phosphate compounds of the instant invention is compared to structurally related, commercial insecticides, i.e., (1) O-(4-bromo-2-chlorophenyl)-O-ethyl-S-propyl phosphorothioate (Curacron) and (2) O-ethyl-O-[4-(methylthio)phenyl] S-propyl phosphorodithioate (Bolstar), on organo-phosphorous and carbamate-resistant two-spotted mites.

TABLE III
RESISTANT MITE COMPARATIVE TEST

| Active Compounds | LD₅₀ Values (ppm) |
|---|---|
| [Structure: CH₃-phenyl-C(CN)=C-(P)*-isopropyl] | 29 |
| [Structure: CH₃-phenyl-C(CN)=C-(P)-CH₂-C(=O)-OC₂H₅] | 37 |
| [Structure: Cl,Cl-phenyl-C(CN)=C-(P)] | 22 |
| [Structure: CH₃-phenyl-C(CN)=C-(P)-isopropyl] | 85 |
| [Structure: Br-phenyl-Cl-(P)] (CURACRON ®) | >500 |
| [Structure: CH₃S-phenyl-O-P(=S)(OC₂H₅)(SC₃H₇)] (Bolstar ®) | >500 |

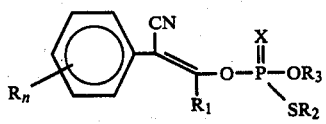

I claim:

1. A method of controlling insects and mites which comprises subjecting them to an insecticidally or miticidally effective amount of a compound of the formula:

[Structure: Rₙ-phenyl-C(CN)=C(R₁)-O-P(=X)(OR₃)(SR₂)]

wherein:
R is hydrogen, C₁ to C₄ alkyl, C₁ to C₄ alkylthio, C₁ to C₄ alkoxy, trihalomethyl, di- or trifluoromethoxy or halogen,
R₁ is hydrogen, unsubstituted or alkyl or halogen substituted cycloalkyl, alkenyl, alkenylcycloalkyl, alkynyl, trihaloalkyl, alkoxycarbonyl, benzyl, C₁ to C₁₀ alkyl, alkoxy C₁ to C₁₀ alkyl, haloalkoxy C₁ to C₁₀ alkyl, alkoxycarbonyl C₁ to C₁₀ alkyl, alkoxyphenyl, haloalkoxyphenyl, or alkoxycarbonylphenyl;
X is oxygen or;
n is 0 to 5; and
R₂ is n-propyl and R₃ is ethyl.

2. A method in accordance with claim 1 wherein:
R is 2—CH₃; and
R₁ is —CH₂—C(CH₃)₂—CH₂CO₂C₂H₅.

3. A method in accordance with claim 1 wherein:
R is 2—CH₃; and
R₁ is —CH₂—CH(CH₃)₂.

4. A method in accordance with claim 1 wherein:
R is 2—CH₃; and
R₁ is —CH(CH₃)₂.

5. A method in accordance with claim 1 wherein:
R is 2—CH₃; and
R₁ is —CH₃.

6. A method in accordance with claim 1 wherein:
R is 2,4-di-Cl; and
R₁ is —CH(CH₃)₂.

7. A method in accordance with claim 1 wherein:
R is 2—CH₃; and

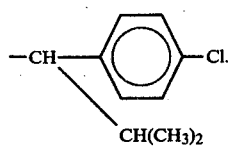

8. Compounds of the formula:

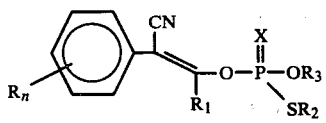

wherein:
R is hydrogen, $C_1$ to $C_4$ alkyl, $C_1$ to $C_4$ alkylthio, $C_1$ to $C_4$ alkoxy, trihalomethyl, di- or trifluoromethoxy or halogen,
$R_1$ is hydrogen, unsubstituted or alkyl or halogen substituted cycloalkyl, alkenyl, alkenylcycloalkyl, alkynyl, trihaloalkyl, alkoxycarbonyl, benzyl, $C_1$ to $C_{10}$ alkyl, alkoxy $C_1$ to $C_{10}$ alkyl, haloalkoxy $C_1$ to $C_{10}$ alkyl, alkoxycarbonyl $C_1$ to $C_{10}$ alkyl, alkoxyphenyl, haloalkoxyphenyl, or alkoxycarbonylphenyl;
X is oxygen;
n is 0 to 5; and
$R_2$ is n-propyl and $R_3$ is ethyl.

9. A compound in accordance with claim 1 wherein:
R is 2—$CH_3$; and
$R_1$ is —$CH_2$—$C(CH_3)_2$—$CH_2CO_2C_2H_5$.

10. A compound in accordance with claim 1 wherein:
R is 2—$CH_3$; and
$R_1$ is —$CH_2$—$CH(CH_3)_2$.

11. A compound in accordance with claim 1 wherein:
R is 2—$CH_3$; and
$R_1$ is —$CH(CH_3)_2$.

12. A compound in accordance with claim 1 wherein:
R is 2—$CH_3$; and
$R_1$ is —$CH_3$.

13. A compound in accordance with claim 1 wherein:
R is 2,4-di-Cl; and
$R_1$ is —$CH(CH_3)_2$.

14. A compound in accordance with claim 1 wherein:
R is 2—$CH_3$; and
$R_1$ is

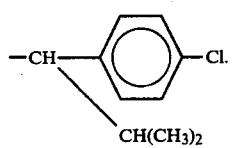

15. An insecticidal and miticidal composition comprising an acceptable carrier and as the active toxicant, a pesticidally effective amount of a compound of the formula:

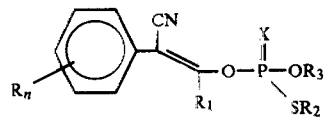

wherein:
R is hydrogen, $C_1$ to $C_4$ alkyl, $C_1$ to $C_4$ alkylthio, $C_1$ to $C_4$ alkoxy, trihalomethyl, di- or trifluoromethoxy or halogen,
$R_1$ is hydrogen, unsubstituted or alkyl or halogen substituted cycloalkyl, alkenyl, alkenylcycloalkyl, alkynyl, trihaloalkyl, alkoxycarbonyl, benzyl, $C_1$ to $C_{10}$ alkyl, alkoxy $C_1$ to $C_{10}$ alkyl, haloalkoxy $C_1$ to $C_{10}$ alkyl, alkoxycarbonyl $C_1$ to $C_{10}$ alkyl, alkoxyphenyl, haloalkoxyphenyl, or alkoxycarbonylphenyl;
X is oxygen or;
n is 0 to 5; and
$R_2$ is n-propyl and $R_3$ is ethyl.

16. A composition in accordance with claim 15 wherein:
R is 2—$CH_3$; and
$R_1$ is —$CH_2$—$C(CH_3)_2$—$CH_2CO_2C_2H_5$.

17. A composition in accordance with claim 15 wherein:
R is 2—$CH_3$; and
$R_1$ is —$CH_2$—$CH(CH_3)_2$.

18. A composition in accordance with claim 15 wherein:
R is 2—$CH_3$; and
$R_1$ is —$CH(CH_3)_2$.

19. A composition in accordance with claim 15 wherein:
R is 2—$CH_3$; and
$R_1$ is —$CH_3$.

20. A composition in accordance with claim 15 wherein:
R is 2,4-di-Cl; and
$R_1$ is —$CH(CH_3)_2$.

21. A composition in accordance with claim 15 wherein:
R is 2—$CH_3$; and
$R_1$ is

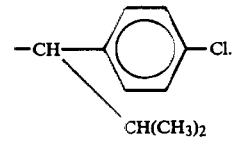

* * * * *

UNITED STATES PATENT AND TRADEMARK OFFICE
CERTIFICATE OF CORRECTION

PATENT NO. : 4,469,688

DATED : September 4, 1984

INVENTOR(S) : Themistocles D.J. D'Silva

It is certified that error appears in the above-identified patent and that said Letters Patent is hereby corrected as shown below:

In the claims, claims 9, 10, 11, 12, 13 and 14, the first line of each, that portion reading "claim 1" should read --claim 8--.

Signed and Sealed this

Twenty-third Day of April 1985

[SEAL]

Attest:

DONALD J. QUIGG

Attesting Officer     Acting Commissioner of Patents and Trademarks